United States Patent [19]

Hasegawa et al.

[11] Patent Number: 4,701,320

[45] Date of Patent: Oct. 20, 1987

[54] COMPOSITION STABLY CONTAINING MINOCYCLINE FOR TREATING PERIODONTAL DISEASES

[75] Inventors: Kenji Hasegawa, Ibaraki; Koichi Nakashima, Takatsuki; Tohru Eguchi, Takatsuki; Masako Ota, Osaka, all of Japan

[73] Assignee: Lederle (Japan), Ltd., Japan

[21] Appl. No.: 801,812

[22] Filed: Nov. 26, 1985

[30] Foreign Application Priority Data

Nov. 29, 1984 [JP] Japan .................................. 59-253877
Nov. 22, 1985 [JP] Japan .................................. 60-263318

[51] Int. Cl.$^4$ .......................... A61K 7/22; A61K 7/16; A61K 33/06
[52] U.S. Cl. ........................................ 424/54; 424/49; 424/154; 514/900
[58] Field of Search ...................... 424/49, 81, 54, 154

[56] References Cited

U.S. PATENT DOCUMENTS

| | | | |
|---|---|---|---|
| 3,017,323 | 1/1962 | Gordon | 424/54 |
| 4,226,848 | 10/1980 | Nagui et al. | 424/19 |
| 4,327,079 | 4/1982 | Aoki et al. | 424/49 |
| 4,454,110 | 6/1984 | Cáslavsk et al. | 424/52 |
| 4,485,089 | 11/1984 | Leipold | 424/49 |

FOREIGN PATENT DOCUMENTS 0049422  4/1982  European Pat. Off. .
1427882  3/1976  United Kingdom .

OTHER PUBLICATIONS

Chem. Abst. 760:135900h (1972)—Triadan
Chem. Abst. 96:196455b (1982)—Haramo et al.
Chem. Abst. 99:98787d (1983)—Berthon et al.
Chem. Abst. 100:96203a (1984)—Golub et al.
Chem. Abst. 102:215162q (1985)—Golub et al.
Ciancio et al.—J. Periodontal. 51(9) (1980), pp. 530–534.
Ciancio et al.—J. Periodontal. 53(9) (1982)—pp. 557–561.
Goodson et al.—J. Periodontal. 54(10) (1983—pp. 575–579.
Addy et al.—J. Periodontal. 53(11) (1982)—pp. 693–699.

*Primary Examiner*—Douglas W. Robinson
*Attorney, Agent, or Firm*—Wegner & Bretschneider

[57] ABSTRACT

A pharmaceutical composition stably containing minocycline for treating periodontal diseases which comprises minocycline or a pharmaceutically acceptable salt thereof and a base composed of a polyhydric alcohol containing a magnesium compound. Optionally, the base can further contain a water soluble high molecular weight compound, ethyl methacrylate/chlrortrimethylammnoniumethyl methacrylate copolymer and its solubilizer. A method for treating periodontal diseases comprising topically applying the composition to the oral cavity is also disclosed.

20 Claims, 6 Drawing Figures

COMPOSITION STABLY CONTAINING MINOCYCLINE FOR TREATING PERIODONTAL DISEASES

FIELD OF THE INVENTION

The present invention relates to a composition for treating periodontal diseases. More particularly, it relates to a composition containing minocycline, one of tetracycline antibiotics, in a stable state. The present invention also relates to a method for treating periodontal diseases by using the composition of the present invention.

BACKGROUND OF THE INVENTION

There are several analogous compounds in tetracycline antibiotics including tetracycline per se as well as minocycline. Since they are very unstable, various studies have been conducted to stably incorporate tetracycline antibiotics into pharmaceutical compositions.

For example, Japanese Patent Laid Open Publication No. 90616/1977 discloses an aqueous injectable solution wherein teteracycline antibiotics such as oxytetracycline, doxycycline, tetracycline, chlortetracycline or a salt thereof is stabilized by chelation with an alkaline earth metal compound such as magnesium compound in an aqueous 2-pyrrolidone solution. Japanese Patent Laid Open Publication No. 94028/1978 discloses a pharmaceutical composition wherein oxytetracycline is stabilized by incorporating it with an alkaline earth metal ion, polyvinyl pyrrolidone and an aliphatic amide such as dimethylacetamide and adjusting pH to 5.0 to 7.5. Further, U.S. Pat. No. 3,335,055 discloses a method for stabilization for tetracycline with magnesium ion and a pyridine derivative such as isonicotinamide.

However, any prior art relating to the stabilization of minocycline can not be found.

By the way, since several years ago, various studies have been conducted to utilize tetracycline antibiotics in the dental field and it has been reported that, when minocycline is administered orally to a patient with a periodontal disease, a high concentration of minocycline in gingival crevicular fluid (GCF) is attained resulting in good healing [J. Periodontal., 51 (9), 530-534 (1980)]. Further, recently, it has been reported that, when minocycline is adminstered orally to a patient with a periodontal disease, an improved change in gingival inflammation and subgingival bacteria resulted [J. Periodontal. 53 (9), 557-561 (1982)].

However, these studies are based on oral administration of minocycline hydrochloride preparations and they are different from topical application of minocycline—per se directly to a lesion in the oral cavity, for example, a gingival inflammation site. Although it has been reported that tetracycline can be incorporated with polyethylmethacrylate or ethylene vinyl acetate to prepare a solid compositionn in the form of strips or fibers to be used for topical application to a lesion in the oral cavity such as periodontal pockets [J. Periodontal., 53 (11), 693-699 (1982) and 54 (10), 575-579 (1983)], this composition is insufficient for treatment and a composition containing minocycline which is suitable for direct topical application has not been found.

On the other hand, in order to treat periodontal diseases, it is desirable to directly and topically apply minocycline to a disease site in the oral cavity such as periodontal pockets to attain a high concentration of minocycline in GCF. However, as mentioned above, minocycline is a very unstable substance and no attempt has been succeeded so far to stably incorporate minocycline into a pharmaceutical composition, particularly, that suitable for topical application.

Accordingly, it has been requested, particularly in the dental field, to stabilize minocycline in a pharmaceutical composition.

Under these circumstances, the present inventors have intensively studied to obtain a pharmaceutical composition stably containing minocycline for treating periodontal diseases, which is suitable for topical application in the oral cavity. As the result, it has been found that minocycline can be stabilized by using a polyhydric alcohol containing a magnesium compound as a base of a composition and, among various tetracycline antibiotics, only minocycline is stabilized by this specific combination. Further, it has been found that the resultant composition is suitable for the treatment of periodontal diseases by topical application thereof in the oral cavity.

OBJECTS AND SUMMARY OF THE INVENTION

One object of the present invention is to provide a pharmaceutical composition containing minocycline in a stable state, particularly, that suitable for treating periodontal diseases, which comprise minocycline or a pharmaceutically acceptable salt thereof, and as a base a polyhydric alcohol containing a magnesium compound.

In this case, optionally, the base of the composition of the present invention which is composed of the polyhydric alcohol containing a magnesium compound can further contain a water soluble high molecular weight compound, a certain methacrylate copolymer and its solubilizer and, in such a case, it has been found that sustained release of minocycline is resulted.

Thus, another object of the present invention is to provide a pharmaceutical composition suitable for treating periodontal diseases which comprises minocycline or a pharmaceutically acceptable salt thereof and a base composed of the polyhydric alcohol, the magnesium compound, the water soluble high molecular weight compound, the methacrylate copolymer and the solubilizer.

Still another object of the present invention is to provide a method for treatment of periodontal disease such as gingival inflammation and the like by using the above pharmaceutical composition containing minocycline in a stable state.

When the base of the above pharmaceutical composition of the present invention contains the water soluble high molecuar weight compound, it is preferable that the base is in the form of a water soluble non-aqueous paste.

Thus, still another object of the present invention is to provide a pharmaceutical composition in the form of a water soluble non-aqueous paste which can directly apply minocycline to a lesion, for example, an inflammation site such as periodontal pockets in the treatment of periodontal disease such as gingival inflammation and the like, and is to provide a method for treating periodontal diseases by using the paste composition.

The above composition containing minocycline in a stable state thus provided by the present invention is particularly suitable for topical application to a lesion in the oral cavity, which has not been studied heretofore in the prior art, and it can be directly applied to a lesion, particularly, a periodontal disease site, for example, periodontal pockets.

Particularly, the composition of the present invention containing the water soluble high molecular weight compound, the methacrylate copolymer and the solubilizer in addition to the combination of the polyhydric alcohol, the magnesium compound and minocycline shows sustained release characteristics of minocycline in addition to excellent stabilization of minocycline. Further, by incorporating the water soluble high molecular weight compound and the methacrylate copolymer in the composition, adhesion of the composition is improved and the active ingredient, minocycline, dissolved in the polyhydric alcohol can be maintained in the form of fine particles and, therefore, minocycline can be maintained in a high concentration in GCF for a long period of time, when the composition is applied to a periodontal disease lesion such as periodontal pockets.

Accordingly, by using the composition of the present invention for treating periodontal diseases, side effects due to oral administration of minocycline such as those of the digestive system, for example, anorexia, nausea and diarrhea, biochemical abnormalities such as thrombocytopenia and eosinophilia or bacterial change can be well prevented and, thereby, the composition is very useful from the clinical point of view.

Thus, in a preferred aspect, the present invention provides a method for treating periodontal diseases which comprises applying the above composition containing minocycline in a stable state to the inside of periodontal pockets.

DETAILED EXPLANATION OF THE INVENTION

Figure 1:
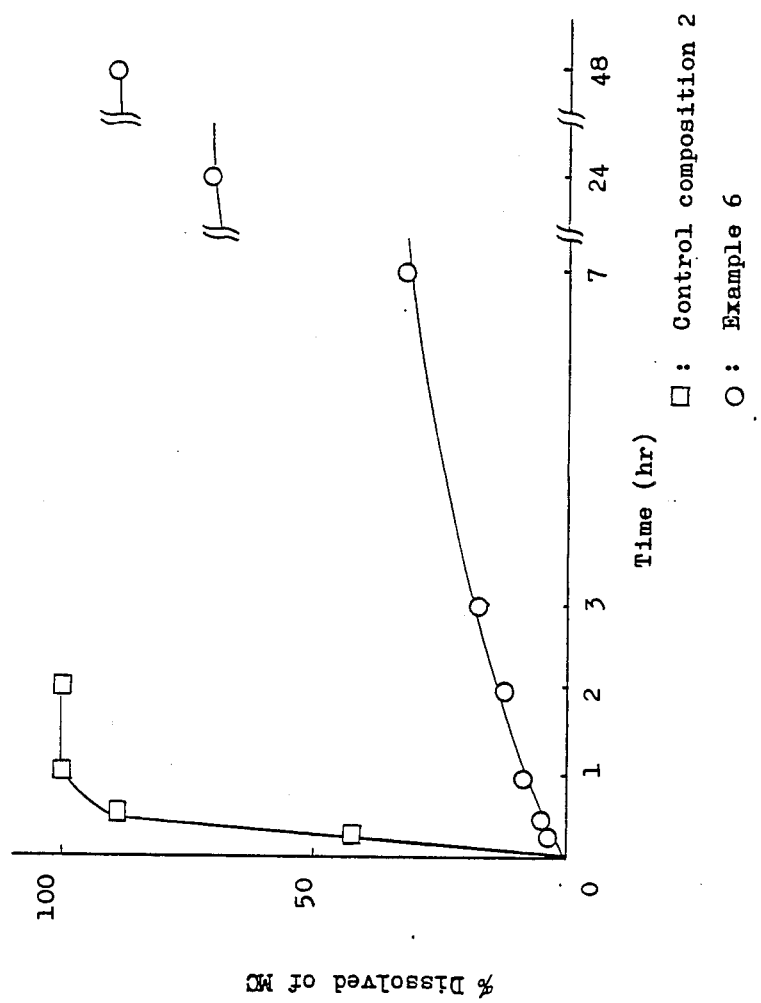
FIG. 1 is a graph illustrating the time-course of the variation in amounts of minocycline released from ointments in a sustained release test hereinafter.

The magnesium compound to be used in the pharmaceutical composition of the present invention may be any pharmaceutically acceptable material, for example, magnesium chloride, magnesium acetate, magnesium sulfate, magnesium carbonate, magnesium gluconate and the like. The magnesium compound can be in the form of its hydrate. Particularly, magnesium chloride is preferred. In general, the magnesium compound is used in an amount of 0.5 to 10% by weight, preferably, 1 to 5% by weight based on the total weight of the composition to obtain improved stabilization of minocycline.

As the polyhydric alcohol, there can be used glycerin, ethylene glycol, diethylene glycol, propylene glycol, dipropylene glycol, hexylene glycol, 1,5-pentanediol, 1,3-butylene glycol and the like. These polyhydric alcohols can be used alone or in combination. For stabilization of minocycline, glycerin is particularly preferred.

Minocycline used in the composition of the present invention may be in the form of the free base or its acid addition salt with a pharmaceutically acceptable acid such as hydrochloric acid, sulfuric acid, trichloroacetic acid and the like. From the point of view of the pharmacological effect, minocycline can be incorporated into the composition in an amount of up to 15% by weight, usually, 0.1 to 5% by weight based on the total weight of the composition, calculated as the free base thereof.

Fundamentally, the composition of the present invention is in the form of viscous liquid or paste wherein minocycline is incorporated into a mixture of the magnesium compound and the polyhydric alcohol. Although the composition can contain up to several percents of water, it is desirable that the composition is in the form of a non-aqueous system in view of the stability of minocycline.

Accordingly, the preferred pharmaceutical composition of the present invention is that containing up to 15% by weight (calculated as the free base) of minocycline or its pharmaceutically acceptable salt based on the total weight of the composition in the base composed of the polyhydric alcohol containing 0.5 to 10% by weight of the magnesium compound based on the total weight of the composition. The more preferred composition is that containing 0.1 to 5% by weight (calculated as the free base) of minocycline or its pharmaceutically acceptable salt based on the total weight of the composition in the base composed of the polyhydric alcohol containing 1 to 5% by weight of the magnesium compound based on the total weight of the composition.

The particularly preferred composition of the present invention is the non-aqueous paste containing 0.1 to 5% (as the free base) by weight of the free base of minocycline or minocycline hydrochloride based on the total weight of the composition in the base composed of glycerin containing 1 to 5% of magnesium chloride based on the total weight of the composition.

As described above, optionally, the composition of the present invention can contain the water soluble high molecular weight compound and, further, the methacrylate copolymer and the solubilizer in the base, in addition to the combination of minocycline, the polyhydric alcohol and the magnesium compound. Particularly, the preferred composition of this second aspect of the present invention comprises a mixture of minocycline or a pharmaceutically acceptable salt thereof, the polyhydric alcohol, the magnesium compound and the water soluble high molecular weight compond, and a mixture of the methacrylate copolymer and the solubilizer.

As the water soluble high molecular weight compound, there can be used those soluble in the polyhydric alcohol, for example, polyvinyl pyrrolidone, polyvinyl alcohol, carrageenan, locust beam gum, guar gum, hydroxyethyl cellulose, xanthan gum, tragacanth gum, starches, succinoglucan and the like. They can be used alone or in combination. Particularly, hydroxyethyl cellulose is preferred for stabilization and sustained release of minocycline. In the composition of the present invention, particularly, the sustained release type composition, the water soluble high molecular weight compound together with the polyhydric alcohol preferably forms a gel and, in order to form a gel, the compound should show suitable thickening effect. In this regard, it is preferable to used the water soluble high molecular weight compound in an amount of 0.2 to 10% by weight based on the total weight of the composition.

The methacrylate copolymer used in the preferred second aspect of the present invention is ethyl methacrylate/chlorotrimethylammoniumethyl methacrylate copolymer. This copolymer is commercially available under the trade name of Eudragit RS. It is considered that the copolymer maintains minocycline dissolved in the polyhydric alcohol in the form of fine particles and, in this regard, it is preferable to use the copolymer in an amount of 0.5 to 10% by weight based in the total weight of the composition.

The solubilizer used is preferably immisible with the polyhydric alcohol. Examples of the solubilizer include esters of lower polyhydric alcohols having 2 to 4 carbon atoms and lower fatty acids having 2 to 4 carbon atoms such as triacetin, tributyrin, ethylene glycol diacetate and the like and esters of lower alcohols having 2 to 4 carbon atoms and dicarboxylic acids having 4 to 10 carbon atoms such as diethyl sebacate, diethyl phthalate, dibutyl phthalate, diisopropyl adipate, dibutyl succinate and the like. They can be used alone or in combination. Particularly, triacetin is preferred. The solubilizer can be used in an amount of 5 to 25% by weight on the total weight of the composition. It has been also found that the stability and sustained release of minocycline can be further improved by using the methacrylate copolymer and the solubilizer in a weight ratio of the copolymer: the solubilizer of from 1:2 to 1:25.

Fundamentally, the composition of the above second aspect of the present invention is in the form of viscous liquid or paste wherein minocycline is incorporated into a mixture of the polyhydric alcohol, the water soluble high molecular weight compound and the magnesium compound, and the methacrylate copolymer and the solubilizer are further incorporated into the resultant mixture. Likewise, in this case, although the composition can contain up to several percents of water, it is also desirable that the composition is in the form of a non-aqueous system in view of the stability of minocycline. Therefore, the composition of the second aspect of the present invention has the following formulation.

| Minocycline or its salt | 0.1–5.0 wt % |
| Water soluble high molecular weight compound | 0.2–10.0 wt % |
| Magnesium compound | 0.5–10.0 wt % |
| Solubilizer | 5.0–25.0 wt % |
| Methacrylate copolymer | 0.5–10.0 wt % |
| Polyhydric alcohol | remainder |

The preferred embodiment of this formulation is as follows.

| Minocycline hydrochloride | 0.1–5.0 wt % |
| Hydroxyethyl cellulose | 0.2–10.0 wt % |
| Magnesium chloride | 0.5–10.0 wt % |
| Triacetin | 5.0–25.0 wt % |
| Eudragit RS | 0.5–10.0 wt % |
| Glycerin | remainder |

The pharmaceutical composition of the present invention can be prepared according to a conventional pharmaceutical technique. For example, the desired composition can be prepared by dissolving the magnesium compound in the polyhydric alcohol and then adding minocycline or a salt thereof to the resultant mixture. If necessary, heating can be effected. Optionally, other ingredients which have no adverse effect on stabilization of minocycline, for example, ethanol, isopropanol and nonionic surfactants may be added. Particularly, in case that the base is prepared without using the methacrylate copolymer, by addition of the above water soluble high molecular weight compound in an amount of 0.2 to 3% by weight based on the weight of the polyhydric alcohol to prepare the composition in the form of a water soluble non-aqueous paste, stabilization of minocycline is further improved and application of the composition is facilitated.

The pharmaceutical composition of the present invention containing the water soluble high molecular weight compound, the methcrylate copolymer and the solubilizer can be also prepared according to a conventional pharmaceutical technique. For example, the magnesium compound and the water soluble high molecular weight compound is dissolved in the polyhydric alcohol and added thereto minocycline or a pharmaceutically acceptable salt thereof to obtain a mixture. A solution of the methacrylate copolymer in the solubilizer is separately prepared and it is added to the above resultant mixture to obtain the desired composition. If necessary, heating can be effected at, for example, 40° to 200° C. The preparation of the composition can be limited to this and the order of addition of the ingredients can be appropriately changed.

The method for treating periodontal diseases with the composition of the present invention can be conducted by topically applying the composition to a periodontal disease site in the oral cavity according to a known manner. In general, the composition is applied in such an amount that the daily dosage of minocycline is 1 to 30 mg (as the free base) for an adult human patient and the composition can be applied daily or weekly, although it depends on degree of periodontal diseases to be treated.

The following Examples, and Experimental and Clinical Tests further illustrate the present invention in detail but are not to be construed to limit the scope thereof.

EXAMPLE 1

| Ingredients | wt % |
| --- | --- |
| Minocycline | 0.1 |
| Magnesium chloride | 0.5 |
| Glycerin | 99.4 |

Magnesium chloride was dispersed and dissolved in glycerin and then minocycline was added to the resulting mixture to obtain the desired composition of the present invention.

EXAMPLE 2

| Ingredients | wt % |
| --- | --- |
| Minocycline hydrochloride | 3.0 |
| Magnesium chloride | 5.0 |

-continued

| Ingredients | wt % |
| --- | --- |
| Glycerin | 92.0 |

According to the same manner as described in Example 1, the desired composition was prepared.

EXAMPLE 3

| Ingredients | wt % |
| --- | --- |
| Minocycline | 1.0 |
| Magnesium acetate | 1.0 |
| Ethylene glycol | 98.0 |

According to the same manner as described in Example 1, the desired composition was prepared.

EXAMPLE 4

| Ingredients | wt % |
| --- | --- |
| Minocycline hydrochloride | 5.0 |
| Magnesium sulfate | 2.5 |
| Propylene glycol | 97.5 |

According to the same manner as described in Example 1, the desired composition was prepared.

EXAMPLE 5

| Ingredients | wt % |
| --- | --- |
| Minocycline hydrochloride | 5.0 |
| Magnesium chloride | 5.0 |
| Glycerin | 89.0 |
| Hydroxyethyl cellulose | 1.0 |

Hydroxyethyl cellulose and magnesium chloride were dispersed in glycerin and dissolved by heating at 100° C. After dissolution, the mixture was cooled to 50° C. and minocycline hydrochloride was added to the mixture. The mixture was homogeneously stirred to obtain the desired composition.

EXAMPLE 6

| Ingredients | wt % |
| --- | --- |
| Minocycline hydrochloride | 3.0 |
| Hydroxyethyl cellulose | 4.0 |
| Magnesium chloride | 5.0 |
| Triacetin | 12.0 |
| Eudragit RS | 2.0 |
| Glycerin | 74.0 |

Hydroxyethyl cellulose and magnesium chloride were dispersed in glycerin and dissolved by heating at 100° C. After dissolution, the mixture was cooled to 50° C. and minocycline hydrochloride was added to the mixture and homogeneously stirred. A solution of Eudragit RS in triacetin was separately prepared and the solution was added to the above resultant mixture to obtain the desired composition.

EXAMPLE 7

| Ingredients | wt % |
| --- | --- |
| Minocycline hydrochloride | 1.0 |
| Carrageenan | 4.0 |
| Magnesium acetate | 5.0 |
| Diethyl sebacate | 10.0 |
| Eudragit RS | 1.0 |
| Glycerin | 79.0 |

According to the same manner as described in Example 6, the desired composition was prepared.

EXAMPLE 8

| Ingredients | wt % |
| --- | --- |
| Minocycline hydrochloride | 3.0 |
| Xanthan gum | 3.0 |
| Magnesium sulfate | 5.0 |
| Diethyl phthalate | 10.0 |
| Eudragit RS | 1.0 |
| Ethylene glycol | 78.0 |

According to the same manner as described in Example 6, the desired composition was prepared.

EXPERIMENTAL TESTS

As mentioned above, according to the present invention, minocycline is stabilized by using the polyhydric alcohol containing the magnesium compound or further containing the water soluble high molecular weight compound, the methacrylate copolymer and the solubilizer as the base, which has not been heretofore in the prior art for stabilization of minocycline. This stabilization effect of the present invention can be demonstrated by the following tests.

(1) Stabilization test of minocycline (No. 1)

According to the formulations shown in Table 1, various compositions containing either minocycline hydrochloride or tetracycline hydrochloride were prepared and stored at 40° C. After storage for 1 month or 3 months, the antibiotic activity of each composition was determined according to the procedure as described in the Japanese Antibiotics Standard Annotate (1982) and the residual rate of activity (%) was calculated from the initial activity of the antibiotic. The results are shown in Table 1.

TABLE 1

| | Composition No. | | | | | | | | | | | | |
| --- | --- | --- | --- | --- | --- | --- | --- | --- | --- | --- | --- | --- | --- |
| | 1 | 2 | 3 | 4 | 5 | 6 | 7 | 8 | 9 | 10 | 11 | 12 | 13 |
| Ingredients (%) | | | | | | | | | | | | | |
| Minocycline HCl | 1 | 1 | 1 | 1 | 0.5 | 0.1 | 1 | 0.1 | 5 | — | — | — | — |
| Tetracycline HCl | — | — | — | — | — | — | — | — | — | 1 | 1 | 1 | 1 |
| $MgCl_2$ | — | 1 | 1 | 1 | — | — | — | 0.5 | 5 | — | 1 | — | — |
| $CH_3COOMg$ | — | — | — | — | 0.5 | — | — | — | — | — | — | 1 | — |
| $MgSO_4$ | — | — | — | — | — | 0.5 | — | — | — | — | — | — | 1 |
| $CaCl_2$ | — | — | — | — | — | — | 1 | — | — | — | — | — | — |
| Distilled Water | — | 98 | — | — | — | — | — | — | — | — | — | — | — |
| Glycerin | 99 | — | 98 | — | 99 | 99.4 | 98 | 99.4 | 90 | 99 | 98 | 98 | 98 |
| Ethylene glycol | — | — | — | 98 | — | — | — | — | — | — | — | — | — |

TABLE 1-continued

| | Composition No. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Residual Rate (%) | | | | | | | | | | | | | |
| 40° C. for 1 month | 55 | 34 | 98 | 97 | 91 | 92 | 54 | 94 | 96 | 20 | 13 | 14 | 13 |
| 40° C. for 3 months | 38 | 13 | 99 | 96 | 85 | 83 | 32 | 90 | 96 | 5 | 3 | 3 | 1 |

As shown in Table 1, stabilization of minocycline can be attained by the combination of the polyhydric alcohol with the magnesium compound and only minocycline is specifically stabilized by this combination.

Further, with regard to Composition Nos. 1 to 3 in Table 1, the amounts of minocycline (MC) and 4-epiminocycline (4-EMC) which is the main decomposition product of minocycline were determined by HPLC according to the procedure described in J. Chromato. Sci., 16, 93–101 (1978). The results are shown in Table 2. In Table 2, the values represent the relative proportions (%) of the amount determined by HPLC to that initially added to the compositions.

TABLE 2

| Composition No. | Immediately after preparation | | After 3 months at 40° C. | |
|---|---|---|---|---|
| | MC | 4-EMC | MC | 4-EMC |
| 1 | 95.9 | 3.4 | 32.6 | 28.5 |
| 2 | 93.2 | 4.4 | 6.8 | 5.6 |
| 3 | 99.2 | 0.7 | 98.9 | 1.0 |

As shown in Table 2, in Composition Nos. 1 and 2 wherein the magnesium compound is not used in combination with the polyhydric alcohol, the proportion of minocycline to 4-epiminocycline is about 1:1 by storage at 40° C. for 3 months and the total amount of both compounds is remarkably decreased in comparison with the amount of minocycline added to the composition. Accordingly, it is considered that minocycline is further converted into other decomposition products. In contrast to this, minocycline is scarcely decomposed in Composition No. 3 which is the composition of the present invention and, therefore, it is considered that conversion thereof into other decomposition products is scarcely taken place in the composition of the present invention. Thus, it is clear that minocycline is stabilized by combination of the magnesium compound and the polyhydric alcohol according to the present invention.

(2) Stabilization test of minocycline (No. 2)

According to the same manner as in the above stabilization test (No. 1), stability of minocycline in the composition of Example 6 and the control compositions of the formulations shown in Table 3 (no triacetin and Eudragit RS were formulated) were tested. The results are shown in Table 4.

TABLE 3

| | Control Composition Nos. | | |
|---|---|---|---|
| | 1 | 2 | 3 |
| Ingredients | | wt % | |
| Minocycline HCl | 3 | 3 | 3 |
| Hydroxyethyl cellulose | 4 | 4 | 4 |
| Glycerin | 93 | 88 | — |
| Distilled water | — | — | 88 |
| Magnesium chloride | — | 5 | 5 |

TABLE 4

| | Example | Control Compositions | | |
|---|---|---|---|---|
| Residual Rate (%) | 6 | 1 | 2 | 3 |
| 40° C. for 1 month | 99 | 59 | 98 | 35 |
| 40° C. for 3 months | 97 | 42 | 99 | 16 |

As is seen from Table 4, the composition containing the water soluble high molecular weight compound and the magnesium compound shows improved stabilization of minocycline and, when the methacrylate copolymer and the solubilizer are added to such a composition, the resultant also shows improved stabilization of minocycline.

In addition to this, as described above, it has been found that the composition of the present invention containing the water soluble high molecular weight compound, the methacrylate copolymer and the solubilizer in combination with the polyhydric alcohol and the magnesium compound has sustained release characteristics and can maintain a high concentration of minocycline in a disease site for a long period of time. The following tests show sustained release characteristics and retention of minocycline in a disease site.

(3) Sustained release characteristics

Each 200 mg of the composition of Example 6 and the above control composition 2 was dispersed in 20 ml of distilled water and the dispersion was incubated at 37° C. The time-course of the variation in the amount of minocycline dissolved was determined by HPLC technique. The results are shown in FIG. 1.

As is seen from FIG. 1, the composition containing the water soluble high molecular weight compound, the methacrylate copolymer and the solubilizer shows sustained release characteristics of minocycline.

(4) Retention of minocycline

Each of the composition of Example 6 and the above control composition 2 was applied in an amount of 50 mg/tooth to periodontal pockets of three patients (male, 29 to 42 years old) and concentrations of minocycline in GCF were determined at 1, 3, 7 and 24 hours after application. The results are shown in FIG. 2.

Figure 2:
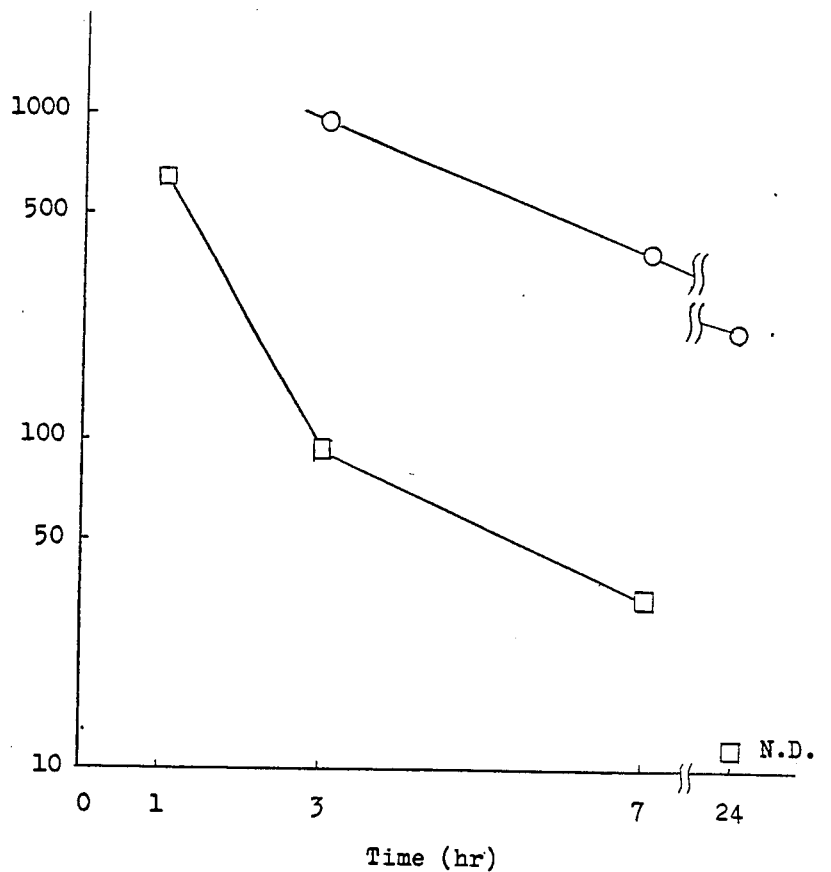
FIG. 2 is a graph illustrating the time-course of the variation in concentrations of minocycline in periodontal pockets in a retention test hereinafter.

As is seen from FIG. 2, the composition of Example 6 maintains a high concentration of minocycline in GCF for several hours. Thus, it is clear that the composition containing the water soluble high molecular weight compound, the methacrylate copolymer and the solubilizer in combination with the polyhydric alcohol, magnesium compound and minocycline has long lasting pharmacological effect. By the way, when a composition containing 3% of minocycline hydrochloride in white petrolatum was subjected to the same test, no release of minocycline was observed.

Clinical Tests

Recently, it has been considered that a peridontal disease, particularly, periodontitis is caused by bacterial infection. That is, it has been understood that periodontitis is an inflammatory disease wherein deposition of dental plaque and calculus is initially observed and then bacteria per se or metabolites thereof in dental plaque and calculus are spread from the gingival periphery to a deep region and that gram negative anaerobic rods are predominant causative bacteria of periodontitis.

Accordingly, in order to treat a periodontal disease, plaque control for removing dental plaque and scaling for removing dental calculus have been employed as an incipient treatment. However, these procedures are insufficient, and it is clear that removal of causative pathogenicd bacteria is a direct causal treatment.

Thus, the pharmaceutical composition stably containing minocycline of the present invention was directly applied to periodontal pockets by microsyringe and the variation of total bacteria therein was observed as follows.

(1) Test 1

(a) Protocol

The minocycline containing composition of the following formulation was prepared and topically applied to periodontal pockets of patients with a periodontal disease (female 5, male 3) by a microsyringe in an amount of 50 mg/tooth. One day, two days and one week after application, bacterial flora in periodontal pockets were observed morphologically. Likewise, as a control, a placebo composition of the same formulation but containing no minocycline was applied and the variation of total bacteria counts in periodontal pockets were observed.

(b) Formulation

| Ingredients | wt % |
| --- | --- |
| Minocycline hydrochloride | 3.0 |
| Magnesium chloride hexahydrate | 5.0 |
| Hydroxymethyl cellulose | 1.5 |
| Glycerin | 90.5 |

(c) Results

By taking the sum of the total bacteria in the periodontal pockets of all the patients in the control group before applying the composition as 100%, the variation of the sum of total bacterial counts in the periodontal pockets of all the patients in both control and test groups were calculated. The results are shown in FIG. 3.

Likewise, variation of motile rods and Spirochetes, which are considered to be good indicators of periodontitis, of the patients in both control and test groups were observed. The results are shown in FIG. 4.

Figure 3:
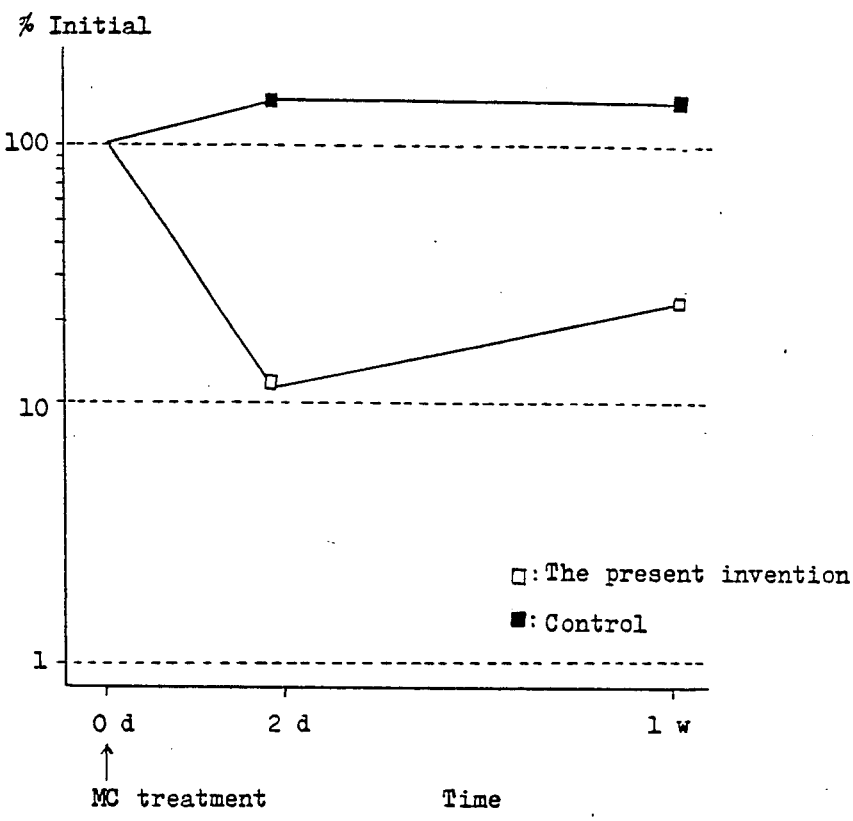
FIG. 3 is a graph illustrating the time-course of the variation in counts of total bacteria in periodontal pockets of patients treated by the composition of the present invention in comparison with that of patients treated with a placebo composition in a treatment test hereinafter.
Figure 4:
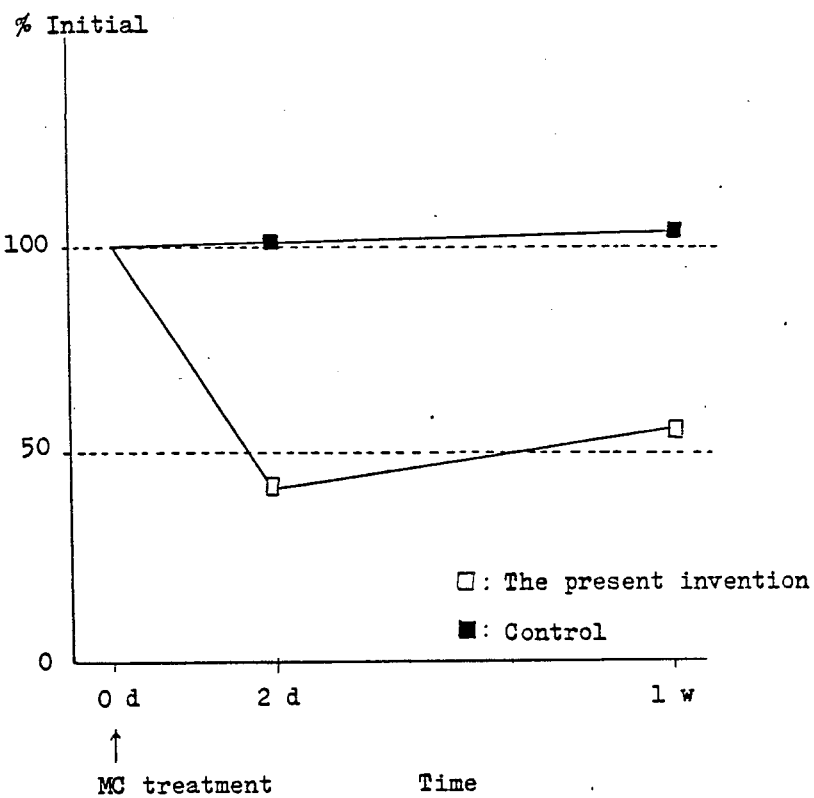
FIG. 4 is a graph illustrating the time-course of the variation in percentages of motile rods and Spirochetes in periodontal pockets of patients in the same treatment test for FIG. 3.

As is seen from the results shown in FIGS. 3 and 4, the pharmaceutical composition stably containing minocycline of the present invention remarkably reduces total bacterial counts and percentages of motile rods and Spirochetes in periodontal pockets and its effect is long lasting.

(2) Test 2

According to the same manner as in Test 1, the following compositions were tested.

(A) Composition of Example 6 (referred to as 3% MINO sustained release)
(B) Above control composition 2 (referred to as 3% MINO solution)
(C) Composition having the same formulation as that of Example 6 provided that no minocycline was added (referred to as placebo sustained release)
(D) Composition having the same formulation as that of control composition 2 provided that no minocycline was added (referred to as placebo solution)

Figure 5:
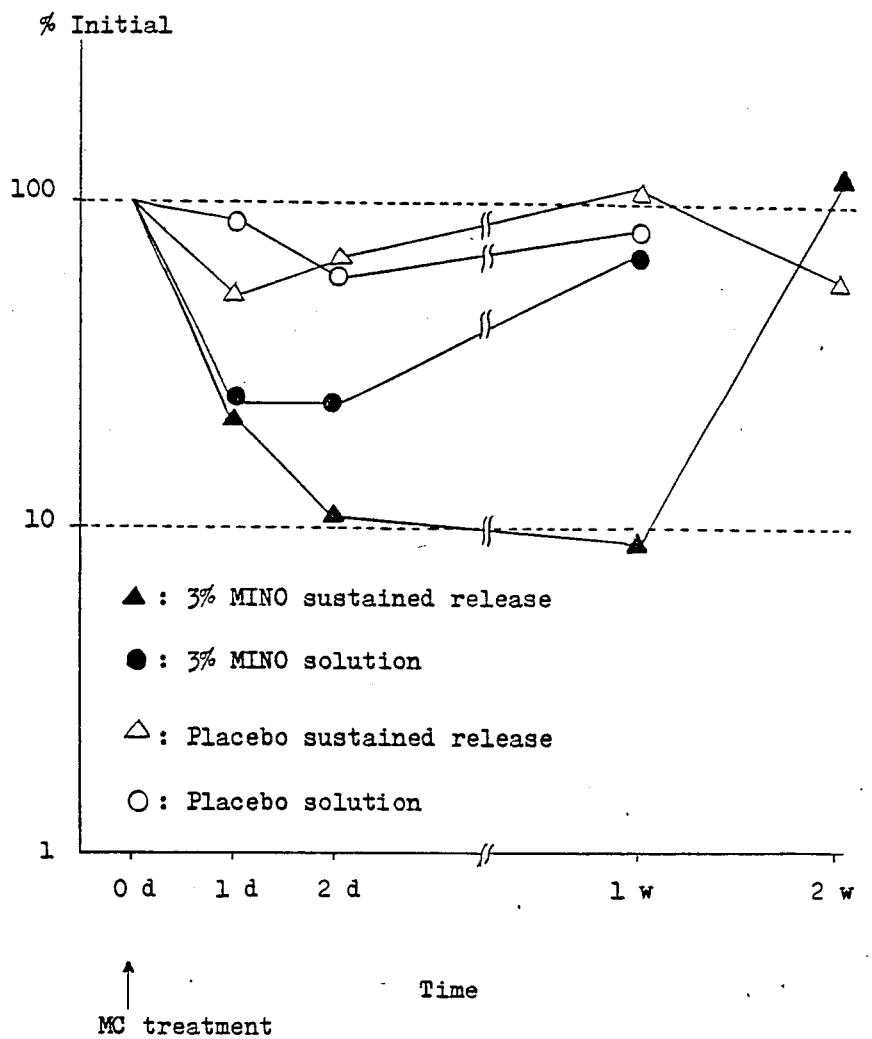
FIG. 5 is a graph similar to that of FIG. 3 and illustrates the results obtained in another similar treatment test hereinafter.
Figure 6:
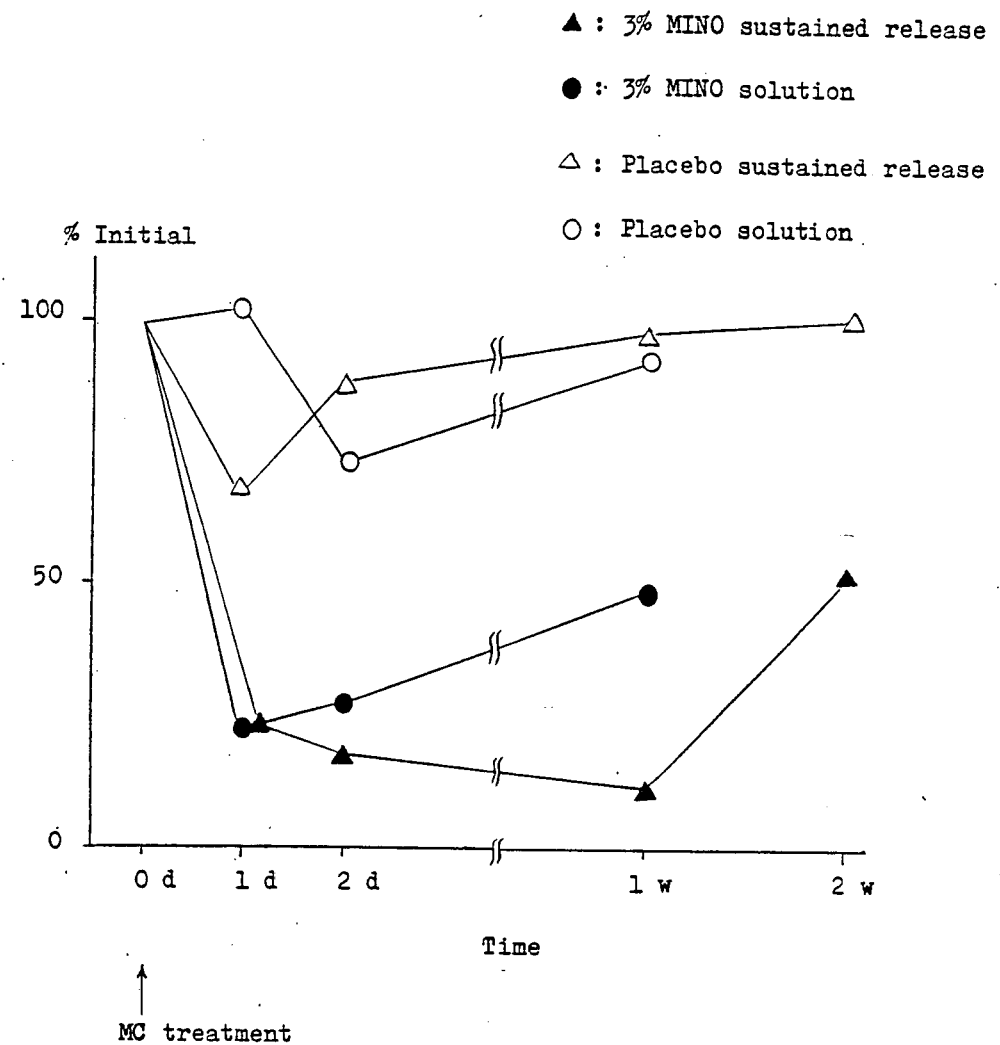
FIG. 6 is a graph similar to that of FIG. 4 and illustrates the results obtained in the same test for FIG. 5.

The variation of the sum of total bacterial counts in the periodontal pockets is shown in FIG. 5 and the variation of motal rods and Spirochetes is shown in FIG. 6. As is seen from FIGS. 5 and 6, the composition of the present invention remarkably reduces total bacterial counts and percentages of motile rods and Spirochetes in periodontal pockets and its effect is long lasting.

(3) Test 3

Further, the effect of the composition of the present invention on particular conditions was clinically tested as follows.

Case 1

The above prepared minocycline containing composition of Example 1 was applied to a periodontal pocket around the left upper molar teeth site of a patient with gingival inflammation (female, 32 years old) once every two days for 2 weeks. Likewise, the above placebo composition was applied to the right upper molar teeth site. Although, before the application, the gingival index of the patient was 2 and the depth of the pocket was 6 mm, the gingival index was reduced to 1 and the depth of the pocket was reduced to 4 mm in the site where minocycline containing composition applied to. In contrast to this, in the site where placebo composition applied to, no change was observed.

Case 2

According to the same manner as in Case 1, the minocycline containing composition of Example 6 and the placebo composition were applied to a patient with gingival inflammation (female, 54 years old) once every week for 2 weeks. As the result, the gingival index was reduced from 2 to 1 and the depth of the pocket was reduced from 5 mm to 4 mm. In contrast to this, no change was observed in the site where the placebo composition was applied to.

Case 3

Brushing and scaling were performed for a patient with alveolar pyorrhea (male, 40 years old). However, conditions such as pus discharge and the like were not improved. Then, the above minocycline containing composition of Example 1 was injected to the lesion. One week after injection, no pus discharge was observed and conditions were remarkably improved.

Case 4

The above minocycline containing composition of Example 1 was topically applied to a patient with acute gingival inflammation and pain (female, 46 years old) once a day for 3 days. As the result, pain was mitigated and redness and swelling of gingiva were disappeared.

No side effect was observed during treatment of these cases.

Thus, the pharmaceutical composition of the present invention remarkably improves clinical conditions of periodontal diseases and provides a useful method for treatment of periodontal diseases.

What is claimed is:

1. A pharmaceutical composition in the form of non-aqueous paste stably containing minocycline for topical application to treat periodontal diseases which comprises:
- (a) 0.1 to 15% by weight of minocycline or a pharmaceutically acceptable salt thereof, and
- (b) a base comprising an alkane-diol or an alkane-triol having 2 to 6 carbon atoms, and 0.5 to 10% by weight of a magnesium compound selected from the group consisting of magnesium chloride, magnesium acetate, magnesium sulfate, magnesium carbonate, magnesium gluconate and hydrates thereof.

2. A pharmaceutical composition according to claim 1, wherein the base (b) further includes
- 0.2 to 10% by weight of a water soluble high molecular weight compound selected from the group consisting of polyvinyl pyrrolidone, polyvinyl alcohol, carrageenan, locust bean gum, guar gum, hydroxyethyl cellulose, xanthan gum, tragacanth gum, starches and succinoglucan;
- 0.5 to 10% by weight of ethyl methacrylate/chlorotrimethylammoniumethyl methacrylate copolymer; and
- 5 to 25% by weight of a solubilizer selected from the group consisting of esters of an alkane-diol or alkane-triol having 2 to 4 carbon atoms and of a lower fatty acid having 2 to 4 carbon atoms and esters of a lower alcohol having 2 to 4 carbon atoms and of a dicarboxylic acid having 4 to 10 carbon atoms.

3. A pharmaceutical composition according to claim 2, wherein minocycline or a pharmaceutically acceptable salt thereof is incorporated into a mixture of the alkane-diol or alkane-triol having 2 to 6 carbon atoms, the magnesium compound, the water soluble high molecular weight compound, ethyl methacrylate/chlorotrimethylammoniumethyl methacrylate copolymer and a solubilizer.

4. A pharmaceutical composition according to claim 3, wherein the composition comprises a mixture of minocycline or a pharmaceutically acceptable salt and a base composed of the alkane-diol or alkane-triol having 2 to 6 carbon atoms, the magnesium compound and the water soluble high molecular weight compound, and a solution of ethyl methacrylate/chlorotrimethylammoniumethyl methacrylate copolymer in the solubilizer.

5. A pharmaceutical composition according to claim 1, wherein the magnesium compound is magnesium chloride or its hydrate.

6. A pharmaceutical composition according to claim 1, wherein the alkane-diol or alkane-triol is a member selected from the group consisting of glycerin, ethylene glycol, diethylene glycol, propylene glycol, dipropylene glycol, hexylene glycol, 1,5-pentanediol and 1,3-butylene glycol.

7. A pharmaceutical composition according to claim 6, wherein the alkane-triol is glycerin.

8. A pharmaceutical composition according to claim 2, wherein the water soluble high molecular weight compound is hydroxyethyl cellulose.

9. A pharmaceutical composition according to claim 2, wherein the solubilizer is a member selected from the group consisting of triacetin, tributyrin, ethylene glycol diacetate, diethyl sebacate, diethyl phthalate, dibutyl phthalate, diisopropyl adipate and dibutyl succinate.

10. A pharmaceutical composition according to claim 9, wherein the solubilizer is triacetin.

11. A pharmaceutical composition according to claim 2, wherein the weight ratio of the methacrylate copolymer: the solubilizer is in the range of 1:2 to 1:25.

12. A pharmaceutical composition according to claim 2, wherein the composition contains 0.2 to 3% by weight of the water soluble high molecular weight compound based on the weight of the polyhydric alcohol.

13. A pharmaceutical composition according to claim 1, wherein minocycline is incorporated into the base composed of glycerin containing magnesium chloride.

14. A pharmaceutical composition according to claim 13, wherein 0.1 to 5% by weight of minocycline based on the total weight of the composition is incorporated into the base composed of glycerin containing 1 to 5% by weight of magnesium chloride based on the total weight of the composition.

15. A pharmaceutical composition according to claim 2, wherein the composition comprises:

| | |
|---|---|
| Minocycline hydrochloride | 0.1–5.0 wt % |
| Hydroxyethyl cellulose | 0.2–10.0 wt % |
| Magnesium chloride | 0.5–10.0 wt % |
| Triacetin | 5.0–25.0 wt % |
| Ethyl methacrylate/chlorotrimethylammoniumethyl methacrylate copolymer | 0.5–10.0 wt % |
| Glycerin | remainder. |

16. A method for topical application of minocycline for treating periodontal diseases which comprises topically applying a pharmaceutical composition in the form of non-aqueous paste stably containing an effective dose of minocycline in the oral cavity, said composition comprising:
- (a) 0.1 to 15% by weight of minocycline or a pharmaceutically acceptable salt thereof, and
- (b) a base comprising an alkane-diol or an alkane-triol having 2 to 6 carbon atoms, and 0.5 to 10% by weight of a magnesium compound selected from the group consisting of magnesium chloride, magnesium acetate, magnesium sulfate, magnesium carbonate, magnesium gluconate and hydrates thereof.

17. A method according to claim 16, wherein the base (b) further includes
- 0.2 to 10% by weight of a water soluble high molecular weight compound selected from the group consisting of polyvinyl pyrrolidone, polyvinyl alcohol, carrageenan, locust bean gum, guar gum, hydroxyethyl cellulose, xanthan gum, traganth gum, starches and succinoglucan;
- 0.5 to 10% by weight of ethyl methacrylate/chlorotrimethylammoniumethyl methacrylate copolymer; and
- 5 to 25% by weight of a solubilizer selected from the group consisting of esters of an alkane-diol or alkane-triol having 2 to 4 carbon atoms and of a lower fatty acid having 2 to 4 carbon atoms and esters of lower alcohol having 2 to 4 carbon atoms and dicarboxylic acid having 4 to 10 carbon atoms.

18. A method according to claim 17, wherein minocycline or a pharmaceutically acceptable salt thereof is incorporated into a mixture of the alkane-diol or alkane-triol having 2 to 6 carbon atoms, the magnesium compound, the water soluble high molecular weight compound, ethyl methacrylate/chlorotrimethylammoniumethyl methacrylate copolymer and the solubilizer.

19. A method according to claim 17, wherein the composition comprises a mixture of minocycline or a pharmaceutically acceptable salt thereof and a base composed of the alkane-diol or alkane-triol having 2 to 6 carbon atoms, the magnesium compound and the water soluble high molecular weight compound, and a solution of ethyl methacrylate/chlorotrimethylammoniumethyl methacrylate copolymer in the solubilizer.

20. A method according to claim 16, wherein the composition is applied to a periodontal pocket.

* * * * *

UNITED STATES PATENT AND TRADEMARK OFFICE
CERTIFICATE OF CORRECTION

PATENT NO. : 4,701,320
DATED : October 20, 1987
INVENTOR(S) : Kenji Hasegawa et al.

It is certified that error appears in the above-identified patent and that said Letters Patent is hereby corrected as shown below:

On the cover page, change the Assignee from "Lederle (Japan), Ltd." to --Sunstar Kabushiki Kaisha and Lederle (Japan), Ltd.--.

Signed and Sealed this

Thirty-first Day of May, 1988

Attest:

DONALD J. QUIGG

*Attesting Officer*

*Commissioner of Patents and Trademarks*